United States Patent [19]

Venturello et al.

[11] Patent Number: 5,108,648
[45] Date of Patent: Apr. 28, 1992

[54] PYRIDINE-3-PEROXYCARBOXYLIC ACID MONOPERSULFATE

[75] Inventors: Carlo Venturello, Novara; Claudio Cavallotti, Milan, both of Italy

[73] Assignee: Ausimont S.r.l., Milan, Italy

[21] Appl. No.: 599,183

[22] Filed: Oct. 17, 1990

Related U.S. Application Data

[60] Division of Ser. No. 448,894, Dec. 12, 1989, Pat. No. 4,994,573, Continuation-in-part of Ser. No. 219,141, Jul. 15, 1988, Pat. No. 4,902,803.

[30] Foreign Application Priority Data

Dec. 13, 1988 [IT] Italy .................. 22923 A/88

[51] Int. Cl.⁵ .................. C01B 15/08; C07D 213/46
[52] U.S. Cl. .................. 252/186.42; 546/315; 546/318; 252/95
[58] Field of Search .................. 546/315, 318; 252/186.42

[56] References Cited

U.S. PATENT DOCUMENTS 4,902,803  2/1990  Venturello .................. 546/318

OTHER PUBLICATIONS

March, J. *Advanced Organic Chemistry*, 3rd Edition, 9-1985, p. 1090.

*Primary Examiner*—Richard D. Lovering
*Assistant Examiner*—Joseph D. Anthony
*Attorney, Agent, or Firm*—Morgan & Finnegan

[57] ABSTRACT

Pyridine-3-peroxycarboxylic acid monopersulfate is herein disclosed, which has the formula:

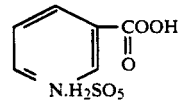

(I)

The process for its preparation and its use as bleaching agent.

1 Claim, No Drawings

PYRIDINE-3-PEROXYCARBOXYLIC ACID MONOPERSULFATE

BACKGROUND OF THE INVENTION

The present invention relates to per se novel pyridine-3-peroxycarboxylic acid monopersulfate having the formula (I):

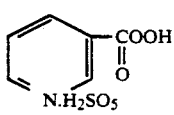

and concerns, mereover, the process for the preparation thereof and the use thereof as bleaching agent.

The pyridine-3-peroxycarboxylic acid monopersulfate having the above defined formula (I) represents a product having a high interest from an industrial viewpoint, with particular reference to the high content of active oxygen per weight unit.

In a more specific way, for example, for example, the pyridine-3-peroxycarboxylic acid monopersulfate having the above defined formula (I) finds a particularly efficacious application in the field of bleaching, in the industry of detergents.

Under this point of view, in the last years, the organic peroxyacids aroused an increasing interest in the industrial field, particularly due to their excellent possibilities for use as bleaching agents in formations for medium low temperature washing, even more widespread due also to energy-saving considerations.

Therefore, the research activity is aimed at finding organic peroxyacid compounds endowed with the necessary requisites of bleaching activity, thermal stability and storage stability or shelf life.

Therefore, many either mono- or di-peroxycarboxyic, straight or cyclic, organic peroxyacids are known and used, among others, in the detergent field.

Already described peroxycarboxylic acids are, e.g.: diperoxydodecanedioic acid, monoperoxyphthalic acid, diperoxyazelaic acid and substituted diperoxyglutaric and adipic acids, etc.

Applicants are not aware of pyridine-3-peroxycarboxylic acid monopersulfate having the above-reported formula (I) nor of any process for its preparation.

The conventional percarboxylation process of hydrogen contemplates carrying out the oxidation of the substrate with a solution of hydrogen peroxide, in concentrated $H_2SO_4$.

The strong acidity of the reaction medium and the presence in the substrate, used as starting material, of a salifiable nitrogen atom of basic character confers to the said substrate a high solubility in the acidic medium, making it impossible to apply any of the conventional processes for the isolation of the peroxycarboxylic acid derivative which may be formed such as by precipitation by dilution with water or by extraction with an organic solvent which is selective for the peroxycarboxylic acid product and is not miscible in the remaining reaction mixture.

Surprisingly, it has been discovered by the applicants that the pyridine-3-peroxycarboxylic acid monopersulfate having the formula (I), salified on the nitrogen atom with the persulfuric acid, subject matter of the present invention, may be obtained by means of a novel process which is also a part of the present invention.

One object of the present invention is to provide, as per se novel compound, the pyridine-3-peroxycarboxylic acid monopersulfate having the above formula (I).

Another object is to provide a simple and cheap process for the preparation of the above peroxycarboxylic acid monopersulfate having the above formula (I).

A further object is the use of the pyridine-3-peroxycarboxylic acid monopersulfate having the above formula (I) as bleaching agent in detergent formulations; and especially those destined for low-medium temperature use.

These, and still other objects which will become even clearer for those skilled in the art from the following detailed disclosure, are achieved, according to the present invention, by the pyridine-3-peroxycarboxylic acid monopersulfate having the above formula (I), and by the relevant preparation process, characterized in that nicotinic acid or pyridine-3-peroxycarboxylic acid or its N-sulfate salt is reacted with $H_2O_2$ in concentrated $H_2SO_4$, and in that the peroxycarboxylic acid monopersulfate (I) is then separated from the reaction mixture by the addition of ethyl acetate.

In this way the peroxycarboxylic acid monopersulfate having the formula (I) is obtained, as a crystalline solid, by means of their insolubilization in the reaction medium by the ethyl acetate solvent.

Described in a somewhat explicit way, the process according to the present invention consists in the peroxycarboxylation reaction of the pyridine-3-peroxycarboxylic acid or of its N-sulfate salt in an acid medium of concentrated $H_2SO_4$, with $H_2O_2$ and in the subsequent addition, at the end of the reaction of ethyl acetate.

This involves the consequent separation of the pyridine-3-peroxycarboxylic acid monopersulfate product having the formula (I), in a stable solid form.

As said above, the pyridine-3-peroxycarboxylic acid substrate used as the starting material may be, optionally, already salified as sulfate on the Nitrogen atom.

The substrate used as the starting material is a compound per se known (nicotinic acid).

The obtained product is then filtered, washed with the solvent, dried and so forth, according to per se known techniques.

According to a preferred operating mode, the reaction of peroxycarboxylation of the pyridine-3-peroxycarboxylic acid, used as the starting substrate, or of its N-sulfate, is carried out by gradually adding $H_2O_2$, having a concentration within the range of from approximately 70% to approximately 90% by weight, to a solution of the substrate in concentrated $H_2SO_4$(96%–98%), by maintaining the reaction temperature throughout the reaction course within the range of 0° C. and 25° C.

Otherwise, it has been found to be operatively possible to prepare in advance the salt of the substrate, in the form of N-sulfate, by processing under the same conditions as shown above, but in the absence of $H_2O_2$, and by separating the thus-obtained salt which is then peroxidized.

The amount of $H_2SO_4$ determined at a concentration of 100%, is substantially equal to 9 moles per mole of substrate.

The hydrogen peroxide is used in an amount which is in excess with respect to the substrate, substantially equal to 5.5 moles per mole of substrate.

The amount of ethyl acetate used is at least equal to 4 liters/substrate mole and furthermore, it is added at a temperature not higher than approximately 40° C.

The pyridine-3-peroxycarboxylic acid monopersulfate product having the formula (I) is usually solid at room temperature. It may be especially useful in formulations of detergent compositions, e.g., granular formulations, as bleaching agents in solution over a wide temperature range.

The detergent compositions may be formulated according to the usual pertinent techniques, together with other components and/or additives, etc.

EXAMPLES

The present invention is now disclosed in still further detail in the following examples, which are supplied for purely illustrative and not limiting purposes.

The pyridine-3-peroxycarboxylic acid monopersulfate was characterized by elemental analysis, by determining its content of active oxygen (by iodometric titration), and by using Fourier Transform Infrared Spectroscopy (FT-IR).

EXAMPLE 1

59.6 g (0.583 mole) of $H_2SO_4$ at 96% were charged into a beaker, equipped with stirrer, thermometer, and outer bath.

The internal temperature was brought to 0° C. and 14.4 g (0.36 mole) of $H_2O_2$ at 85% were slowly added under stirring, so that the temperature was maintained lower than 5° C.

8 g (0.0650 mole) of pyridine-3-peroxycarboxylic acid (Nicotinic acid) were then gradually added and the reaction was continued for 4 hours at 20° C./25° C.

At the end, the reaction mixture was poured into 250 ml of ethyl acetate maintained under stirring at between −10° C. and 0° C.

After 2 hours of reaction at this temperature, the crystalline product was filtered under vacuum and over a porous septum. The product was directly washed on the filter with ethyl acetate (50 ml), then with ethyl ether (50 ml), and then dried on $CaCl_2$ under vacuum and at room temperature for 1 hour.

12.5 g of crystalline product were obtained having an active oxygen content of 11.75% (theoretic value for pyridine-3-peroxycarboxylic acid monopersulfate; 12.64%). Yield 70%.

ELEMENTAL ANALYSIS:

Computed for $C_6H_7O_8NS$: C=28.47%; H=2.78%; N=5.53%; O (active)=12.64%; $H_2SO_5$=45.07%.
Found: C=28.90%; H=2.86%; N=5.69%; O (active)=11.75%; $H_2SO_5$=42.30%.
Melting Point: 85° C. (with decomposition).

EXAMPLE 2

APPLICATION EXAMPLE

BLEACHING WITH PYRIDINE-3-PEROXYCARBOXYLIC ACID MONOPERSULFATE

Bleaching tests were carried out with a detergent formulation containing pyridine-3-peroxycarboxylic acid monopersulfate (composition A) in the amount reported in the following Table 1, as compared to a similar formulation containing, as bleaching agent, H 48 per acid (Mg salt of monoperphthalic acid, a commercial known peroxyacid, manufactured by INTEROX Chemical Ltd London, U.K. to be used in the detergent art) (composition B).

Compositions A and B were obtained by dry blending of a detergent base, common for all the compositions, which will be better defined hereinafter, with the above listed bleaching agents. As detergent base, a granular composition was used containing all the conventional components of a detergent for washing machines (surfactants, builders and so forth), except the chemical bleaching agents, and obtained by atomization of the component mixture.

The used detergent base had the following composition:

|  | Weight % |
|---|---|
| Total surfactants | 15.4 |
| Sodium alkyl ($C_{12}$) Benzensulphonate, soap, ethoxylated (EO) alcohol ($C_{16}$–$C_{18}$) | |
| Total sodium phosphates | 8.8 |
| Zeolite A | 19.8 |
| Silicate ($SiO_2/Na_2O$ = 2) | 4.4 |
| Sodium sulphate | 36.6 |
| Sodium carbonate | 6.6 |
| Carboxymethylcellulose | 1.1 |
| Anti-incrusting copolymers | 4.8 |
| Water | 2.2 |
| Optical bleaching agents | 0.3 |

The metering of the compositions A and B was carried out in such a way to introduce into the washing machine a constant amount of detergent base corresponding to 120 g and such an amount of bleaching agent to introduce into the washing machine a quantity of total initial active oxygen equal to about 2 g of oxygen for each washing cycle, for all the operations.

Therefore, the proportions of the compositions A and B, reported in the following Table I, were used in the bleaching tests.

TABLE 1

| Composition A | |
|---|---|
| Detergent base | 120 g |
| Pyridine-3-peroxycarboxylic acid monopersulfate haveing 11.1% of active oxygen | 18 g |
| Composition B | |
| Detergent base | 120 g |
| H 48 having 5.5% of active oxygen | 39 g |

The tests were carried out by a commercial IGNIS Mod. 644 washing machine by introducing into the machine two cotton specimens 15×15 cm stained with standard stains of red wine at EMPA INSTITUTE of St. Gallo (Switzerland) and marked with the "EMPA 114" mark, together with 3 Kg of cleaned cotton wipers as ballast for each washing operation.

The washings were carried out with a conventional program at low temperature (about 40° C.). The normal water of pipeline network was used, having a hardness of 14° F.

The results of the tests are reported in the following Table 2, wherein the data are expressed as bleaching %, defined as:

$$\text{Bleaching \%} = \frac{A - B}{C - B} \times 100$$

wherein:

A = degree of whiteness (%) of the specimen bleached after the test;
B = degree of whiteness (%) of the specimen before the test;
C = degree of whiteness (%) of the completely bleached specimen and wherein the degrees of whiteness were measured by means of an Elrepho Zeiss reflectometer, assuming MgO = 100% of whiteness, and using filter N. 6 ($\lambda = 464$ nm).

TABLE 2

| Bleaching % | |
|---|---|
| Composition A | 57 |
| Composition B | 52 |

The data show the higher bleaching activity of the claimed peroxyacid in comparison with that of H 48.

EXAMPLE 3

APPLICATION EXAMPLE

Bleaching tests were carried out with the novel pyridine-3-peroxycarboxylic acid monopersulfate at an acid pH, as compared to H 48 (Mg salt of monoperphthalic acid), a commercial peroxyacid known in the detergent art, and manufactured by INTEROX Chemical Ltd., London, U.K.

The results are listed in the following Table 3.

All tests were carried out at constant temperature of 60° C. with an initial concentration of total active oxygen in the bleaching solution equal for all products, and equal to 200 mg/l.

Process

For each test, 500 ml of deionzed water, contained in a 1,000 ml flask, equipped with a condenser, were heated to a temperature of 60° C.

The bleaching product was dissolved by stirring the amounts thereof added as shown in the following Table 3. Immediately thereafter, two cotton specimens of 10 × 10 cm stained with standard stains of red wine at EMPA INSTITUTE of St. Gallo (Switzerland), and marked with the "EMPA 114" mark, were added to the solution having a pH value of 3-4.

The system was subsequently kept stirred for 60 minutes, and, at the end of this time, the specimens rinsed under running water, were dried and ironed, and where them submitted to the evaluation of the bleaching effect by measuring the degree of whiteness by reflectometry. The results are reported in the following Table 1, wherein the data were expressed as bleaching %, as defined in Example 2.

The data listed Table 3, show that the peroxyacids of the present invention, in acid solution, have a bleaching activity particular high (this is particularly surprising in consideration of the fact that the peroxyacid compounds generally show a bleaching activity very modest in this condition) and very much higher than that of H 48 product.

TABLE 3

| | Tests Carried out at Acid pH (3-4) | | |
|---|---|---|---|
| Compound | Amounts used in the tests (grams) | Initial concentration of total active oxygen (mg/l) | % Bleaching at 60° C. |
| Example 1 (TITER = 11.75% of active oxygen) | 0.86 | 200 | 74.0 |
| H 48 (TITER = 5.5% of active oxygen) | 1.86 | 200 | 60 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above mentioned references are hereby incorporated by reference.

We claim:

1. Method of bleaching comprising adding pyridine-3-peroxycarboxylic acid monopersulfate having formula (I)

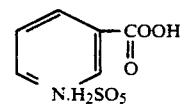

as bleaching agent to detergent formulations.

* * * * *